(12) United States Patent
Lin et al.

(10) Patent No.: US 8,879,065 B1
(45) Date of Patent: Nov. 4, 2014

(54) SYSTEMS AND METHODS FOR LOCALIZED SURFACE PLASMON RESONANCE SENSING

(75) Inventors: Yongbin Lin, Huntsville, AL (US); Robert Lindquist, Madison, AL (US); Yang Zou, Huntsville, AL (US)

(73) Assignee: The Board of Trustees of the University of Alabama for and on behalf of the University of Alabama in Huntsville, Huntsville, AL (US)

( * ) Notice: Subject to any disclaimer, the term of this patent is extended or adjusted under 35 U.S.C. 154(b) by 97 days.

(21) Appl. No.: 13/104,719

(22) Filed: May 10, 2011

(51) Int. Cl.
*G01N 21/00* (2006.01)
*G01N 21/55* (2014.01)

(52) U.S. Cl.
USPC .......................................... 356/445; 356/326

(58) Field of Classification Search
CPC  G01N 21/554; G01N 21/7703; G01N 21/658
USPC .................. 356/445, 301, 317, 326; 385/129; 435/281.1; 436/525
See application file for complete search history.

(56) References Cited

U.S. PATENT DOCUMENTS

| | | | |
|---|---|---|---|
| 5,363,463 A * | 11/1994 | Kleinerman | 385/123 |
| 7,113,624 B2 * | 9/2006 | Curry | 382/132 |
| 7,638,345 B2 * | 12/2009 | Lee et al. | 438/27 |
| 7,999,353 B1 * | 8/2011 | Odom et al. | 257/618 |
| 2003/0147081 A1 * | 8/2003 | Inamoto et al. | 356/445 |
| 2004/0174521 A1 * | 9/2004 | Drachev et al. | 356/301 |
| 2006/0038990 A1 * | 2/2006 | Habib et al. | 356/301 |
| 2007/0004026 A1 * | 1/2007 | Barbour | 435/283.1 |
| 2008/0099667 A1 * | 5/2008 | Stark et al. | 250/227.18 |
| 2010/0178713 A1 * | 7/2010 | Nishiuma et al. | 436/525 |
| 2011/0019186 A1 * | 1/2011 | Himmelhaus et al. | 356/317 |
| 2011/0176130 A1 * | 7/2011 | Gu et al. | 356/301 |
| 2011/0208031 A1 * | 8/2011 | Wolfe et al. | 600/378 |

FOREIGN PATENT DOCUMENTS

JP        59086017 A  *  5/1984

OTHER PUBLICATIONS

Lin, et al., "Demonstration of an ultra-wideband optical fiber inline polarizer with metal nano-grid on the fiber tip," Optics Express 17849, vol. 17, No. 20, Sep. 28, 2009.

* cited by examiner

*Primary Examiner* — Sang Nguyen
(74) *Attorney, Agent, or Firm* — Maynard Cooper & Gale, P.C.; Jon E. Holland (57) ABSTRACT

Embodiments of the present disclosure generally pertain to systems and methods for localized surface plasmon resonance (LSPR) sensing. A system in accordance with an exemplary embodiment of the present disclosure comprises an optical fiber having a metallic dot array on a tip of the optical fiber, a light source coupled to the optical fiber via a light coupler, and a spectrometer coupled to the optical fiber via the coupler. The light source is configured to transmit light within a range of wavelengths along the optical fiber. When the light reaches the dot array, the light excites surface plasmons of the dot array and causes the surface plasmons of the dots to resonate. The dots are chemically functionalized to have a specific affinity for a particular substance, and the resonance frequency of the dots changes when the substance is present thereby changing an absorption peak of the light. The light is reflected back through the optical fiber to the spectrometer, and the spectrometer detects a parameter indicative of a change in the absorption peak. Presence of the particular substance is determined based upon the change in the absorption peak.

10 Claims, 7 Drawing Sheets

SYSTEMS AND METHODS FOR LOCALIZED SURFACE PLASMON RESONANCE SENSING

RELATED ART

Localized surface plasmon resonance (LSPR) involves excitation of surface plasmons of nanometer-sized metallic structures, or dots, by light. LSPR for metallic dots is typically used in chemical and biochemical sensing applications in order to provide high sensitivity sensing capabilities. In such applications, a resonant oscillation of the conduction of electrons within the metallic nanostructures gives rise to enhanced scattering and absorption of light. The spectra position of the light is dependent on the size and shape of the dots, the composition of the dots, and the interaction between the dots and the dielectric environment surrounding the dots. By detecting the spectra position of the light, it is possible to determine which substances make up the dielectric environment surrounding the dots.

Typical LSPR sensors involve positioning metallic dots on surfaces of planar substrates, such as, for example, glass or sapphire substrates. However, such LSPR sensors are often relatively expensive to manufacture, difficult to use, bulky, and difficult to transport.

BRIEF DESCRIPTION OF THE DRAWINGS

The disclosure can be better understood with reference to the following drawings. The elements of the drawings are not necessarily to scale relative to each other, emphasis instead being placed upon clearly illustrating the principles of the disclosure. Furthermore, like reference numerals designate corresponding parts throughout the several views.

DETAILED DESCRIPTION

Embodiments of the present disclosure generally pertain to systems and methods for localized surface plasmon resonance (LSPR) sensing. A system in accordance with an exemplary embodiment of the present disclosure comprises an optical fiber having a metallic dot array on a tip of the optical fiber, a light source coupled to the optical fiber via a light coupler, and a spectrometer coupled to the optical fiber via the coupler. The light source is configured to transmit light within a range of wavelengths along the optical fiber. When the light reaches the dot array, the light excites surface plasmons of the dot array and causes the surface plasmons of the dots to resonate. The dots are chemically functionalized to have a specific affinity for a particular substance, and the resonance frequency of the dots changes when the substance is present thereby changing an absorption peak of the light. The light is reflected back through the optical fiber to the spectrometer, and the spectrometer detects a parameter indicative of a change in the absorption peak. Presence of the particular substance is determined based upon the change in the absorption peak.

Figure 1:
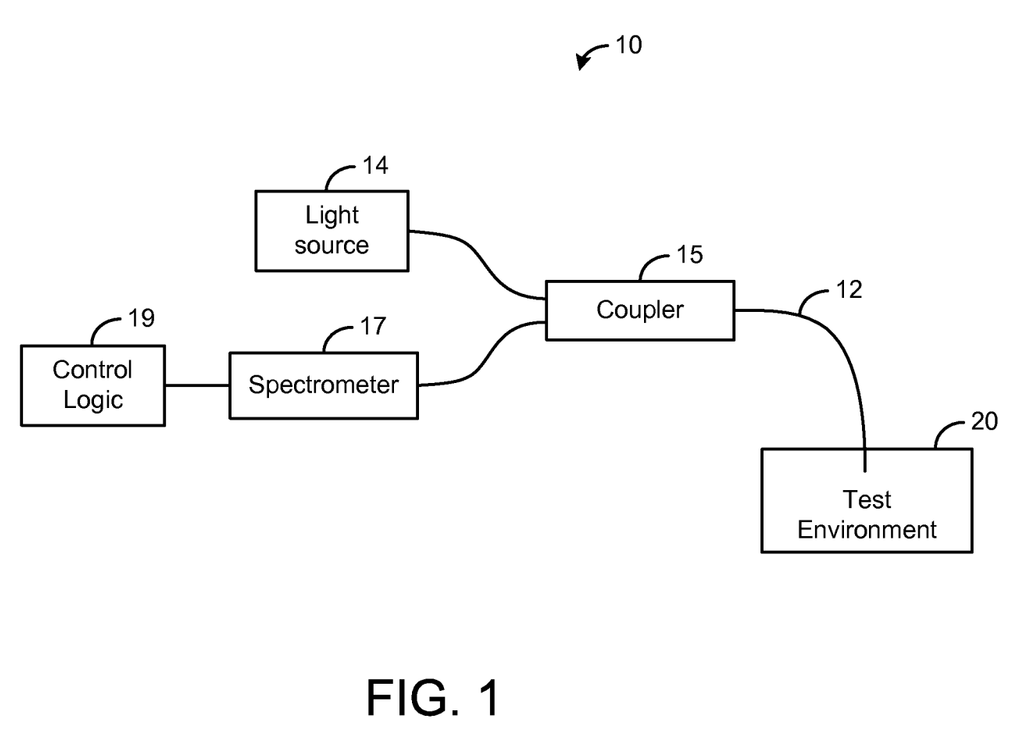
FIG. 1 is a block diagram illustrating an exemplary LSPR sensing system in accordance with the present disclosure.

FIG. 1 depicts an exemplary LSPR sensing system 10. The LSPR sensing system 10 comprises an optical fiber 12, a light source 14, a light coupler 15 (e.g., a beam splitter), a spectrometer 17, and control logic 19. The light source 14 is coupled to the optical fiber 12 via the coupler 15. The spectrometer 17 is also coupled to the optical fiber 12 via the coupler 15, and the spectrometer 17 is coupled to the display device 19. The light source 14 is configured to transmit light having a range of wavelengths (e.g., white light) along the optical fiber 12 via the coupler 15. In one embodiment, the light source 14 comprises a tungsten halogen white light source, although other types of light sources are possible in other embodiments. The light is reflected at the end of the fiber 12 and is received by the spectrometer 17.

The optical fiber 12 extends from the coupler 15 to a test environment 20. The test environment 20 may comprise any environment for which chemical or biochemical sensing is desired, such as, for example, air, water or other liquid substance, or the human body. Such test environment 20 may contain harmful or otherwise significant chemical or biochemical substances for which detection is desirable. The optical fiber 12 has a metallic dot array (not shown in FIG. 1), discussed in more detail hereafter, located on a tip of the optical fiber 12. The optical fiber 12 transmits reflected light indicative of detected substances in the test environment 20 to the spectrometer 17. In one embodiment, the optical fiber 12 is configured to transmit the light received from the light source 14 via the coupler 15 to the test environment 20, and to transmit reflected light having an absorption peak based on the array to the spectrometer 17 via the coupler 15. The absorption peak occurs at the wavelength for which a maximum amount of the light is absorbed or scattered and a minimum amount of the light is reflected. Note that the optical fiber 12 is relatively lightweight and small in diameter, which allows the optical fiber 12 to reach various test environments 20 which conventional LSPR sensors are unable to reach or have a difficult time reaching.

The spectrometer 17 is configured to receive the reflected light from the optical fiber 12 via the coupler 15, to measure the properties of the reflected light, and to provide a data indicative of such properties to the control logic 19. For example, in one embodiment, the spectrometer 17 measures the position of the absorption peak of the reflected light and transmits a signal indicative of such position to the control logic 19. Based on the wavelength of the absorption peak, the control logic 19 determines whether a substance of interest is present in the test environment 20 and also the concentration or amount of such substance in the test environment 20. For example, in one exemplary embodiment, the control logic 19 determines the extent to which the absorption peak shifts when the tip of the optical fiber 12 is exposed to the test environment 20 and, based on such information, determines whether and to what extent the substance of interest is present in the test environment 20. The control logic 19 then displays such information to a user. Accordingly, a high sensitivity LSPR sensor is provided.

Note that the control logic 19 may be implemented in hardware, software, firmware or any combination thereof. In one exemplary embodiment, such as is depicted by FIG. 13, the control logic 19 is implemented in software and stored within memory 21 of a computer system 22.

Figure 13:
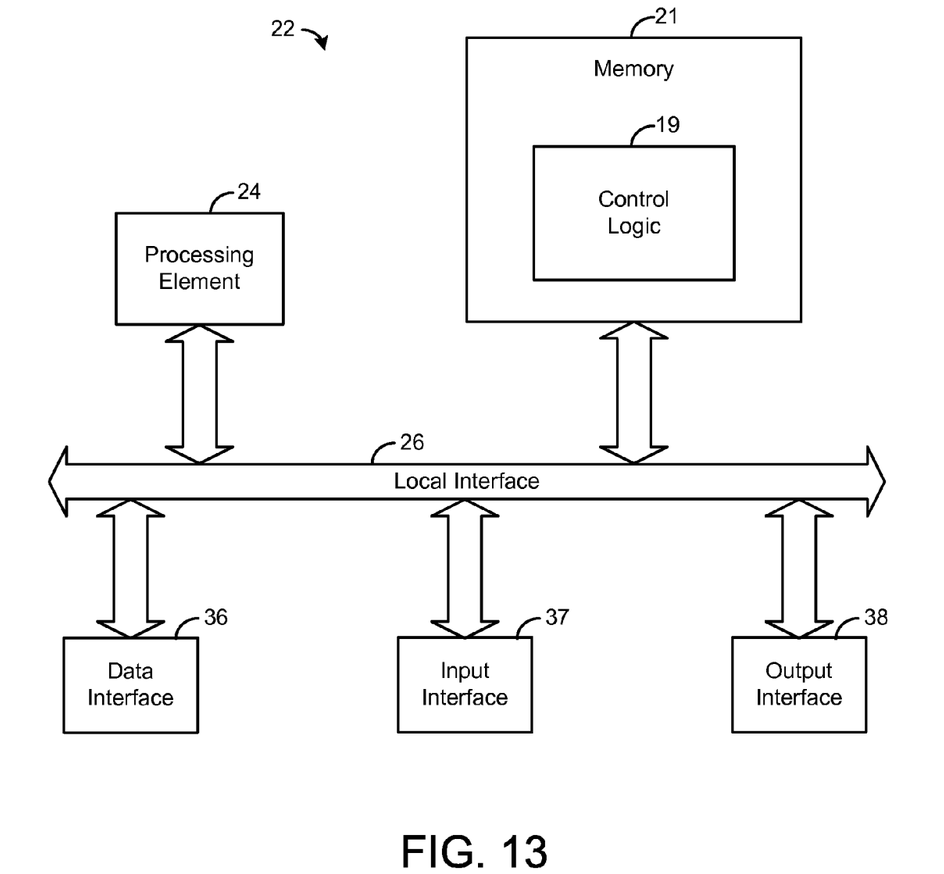
FIG. 13 depicts an exemplary embodiment of a computer system for storing and executing control logic, such as is depicted by FIG. 1.

The exemplary embodiment of the computer system 22 depicted by FIG. 13 comprises at least one conventional processing element 24, such as a digital signal processor (DSP) or a central processing unit (CPU), that communicates to and drives the other elements within the system 22 via a local interface 26, which can include at least one bus. Furthermore, a data interface 36 is coupled to and enables communication with the spectrometer 17 (FIG. 1). In addition, an input interface 37, for example, a keyboard, keypad, or a mouse, can be used to input data from a user of the system 22, and an output interface 38, for example, a printer or a display device, e.g., a liquid crystal display (LCD), can be used to output data to the user. In one exemplary embodiment, the control logic 19 displays via the output interface 38 the analysis results (e.g., indicating whether and/or to what extent a substance of interest is present in the test environment 20).

Figure 2:
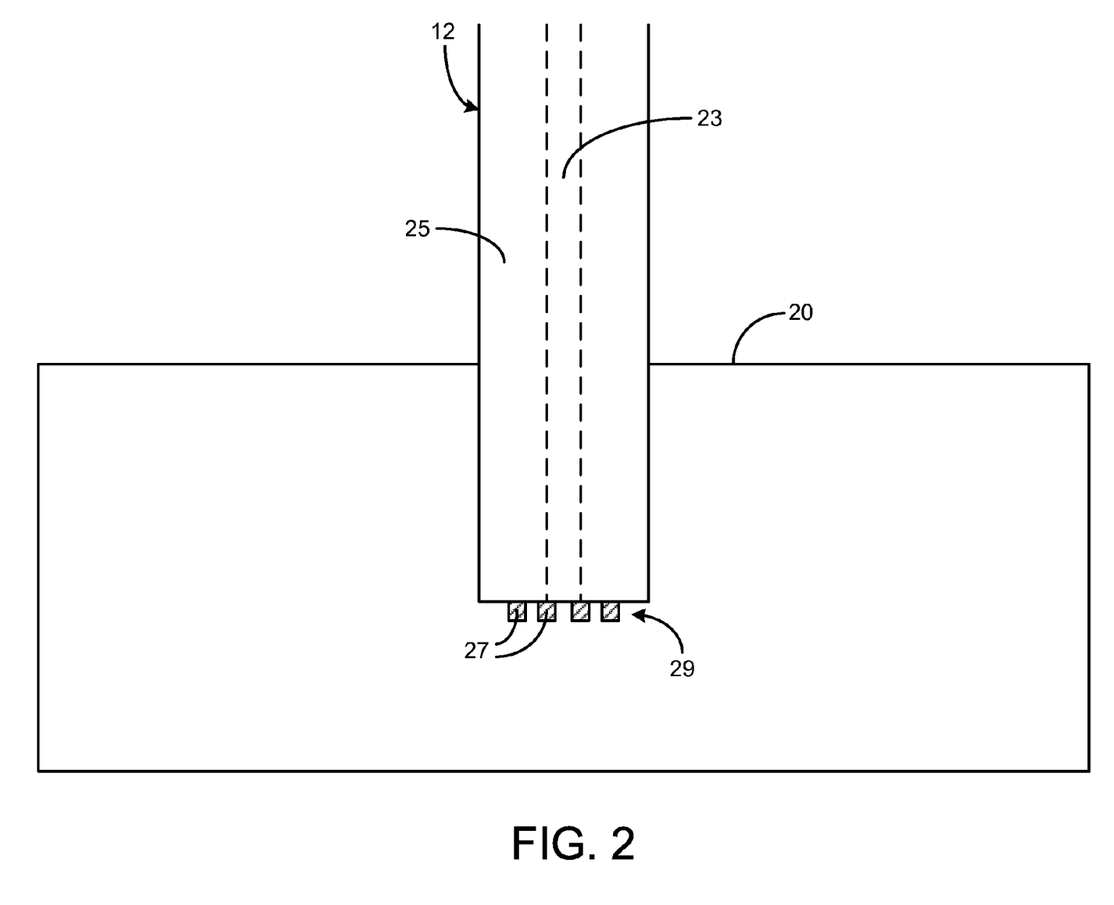
FIG. 2 depicts a side view of an optical fiber depicted in FIG. 1.

FIG. 2 depicts a side view of the optical fiber 12 of FIG. 1 with the tip of the fiber 12 positioned in the test environment 20. The optical fiber 12 comprises a cylindrical core 23 surrounded by cladding 25. In one embodiment, the optical fiber 12 comprises single mode silica optical fiber, although other types of optical fibers are possible in other embodiments. In one embodiment, the core 23 has a diameter of approximately 9 micrometers ($\mu m$) and the cladding 25 has a diameter of approximately 125 $\mu m$. However, other dimensions are possible in other embodiments. The refractive index of the cladding 25 is lower than that of the core such that light is guided through the core 23. As shown by FIG. 2, the optical fiber 12 has a cleaved tip which creates a flat surface at an end of the optical fiber 12. A plurality of metallic dots 27 are fabricated on the tip of the optical fiber 12, forming a dot array 29. In one embodiment, the dots 27 are composed of gold, although other types of materials are possible in other embodiments. The dot array 29 is positioned over the core 23 such that the light propagating through the core 23 strikes the dots 27.

The dot array 29 is designed to have a certain affinity for a particular substance which may be present in the test environment 20. Upon binding with such substance, the surface resonance frequency of the dot array 29 changes, causing the dot array 29 to exhibit different optical characteristics. The size, spacing, and composition of the dots 27, along with the interaction between the dots 27, chemical functionalization of the dots 27 and/or substances in the test environment 20, determine the position of the absorption peak. In one exemplary embodiment, such parameters of the dots 27 are selected so that the dot array 29 will have an affinity for a particular substance of interest. Specifically, as will be described in more detail hereafter, the parameters are selected such that an absorption peak due to surface plasmon resonance shifts by a specific amount when the substance of interest binds with the dots 27 depending on the concentration or amount of the substance that binds to the dots 27.

When the light in the core 23 reaches the dot array 29, the illumination by the light excites surface plasmons of the dots 27 and causes surface plasmons of the dots 27 to resonate. The absorption peak of the light reflected back through the core 23 depends on the resonance frequency of the dots 27. Thus, when the substance of interest is present in the test environment, the substance binds with the dots 27 and changes the resonance frequency of the dots 27 thereby changing the wavelength of the absorption peak of the reflected light. Specifically, the amount of the substance that binds to the dots 27 is a function of the composition and the size and spacing of the dots 27. The absorption peak of the reflected light is then detected by the spectrometer 17, and the control logic 19 analyzes the detected absorption peak to determine whether and to what extent the substance of interest is present in the test environment 20. In one exemplary embodiment, the control logic 19 determines the amount that the absorption peak shifts when introduced to the test environment 20 from an environment that is free of the substance of interest and determines the concentration or amount, if any, of the substance that is present in the test environment based on the extent of the absorption peak shift. If the substance of interest is not present in the test environment 20, the resonance frequency of the dots 27 does not change, and there is no shift of the measured absorption peak. However, if the substance of interest is present in the test environment, then the absorption peak shifts by an amount depending on the concentration of the substance in the test environment and the configuration of the dot array 29.

Figure 3:
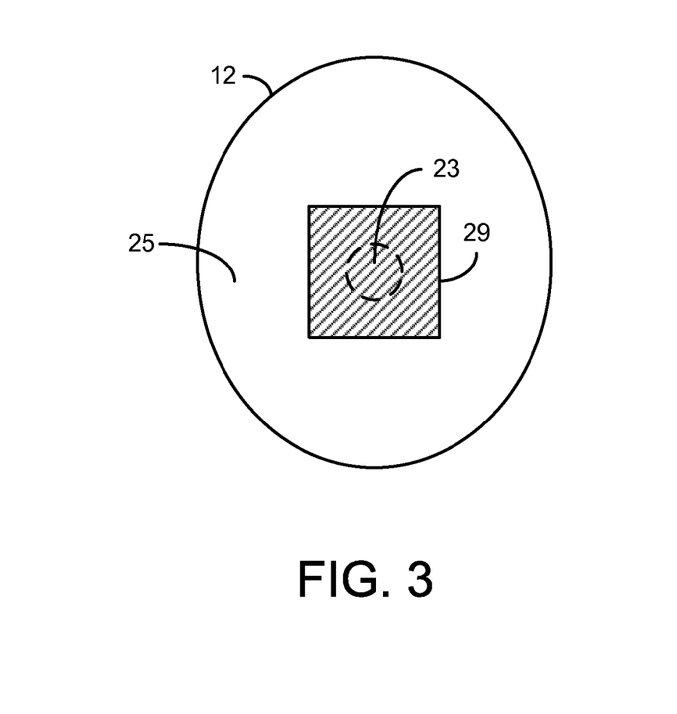
FIG. 3 depicts an end view of a tip of the optical fiber of FIG. 2.

FIG. 3 depicts an end view of the tip of the optical fiber 12 of FIG. 1. As shown by FIG. 3, the dot array 29 is positioned over the core 23 on the tip of the optical fiber 12. In one embodiment, the dot array 29 is a 40 $\mu m$ by 40 $\mu m$ square, although the array 29 may have other shapes and sizes in other embodiments. As set forth above, in one embodiment, the dot array 29 is composed of gold, which demonstrates high surface plasmon excitation and bio-compatibility, and is resistant to oxidation degradation. However, other materials are possible in other embodiments. The dot array 29 has an affinity for a particular substance. When the light reaches the dot array 29, the illumination from the light causes excitation of surface plasmons of the array 29 thereby causing the surface plasmons to resonate. The dot array 29 is configured such that the dots 27 bind with the substance of interest thereby changing the resonance frequency of the surface plasmons. Thus, the wavelength of the absorption peak of the light reflected into the core 23 is shifted when the particular substance of interest is present in the environment 20. The extent of the shift is indicative of the concentration or amount of the substance present in the environment 20. Generally, the shift is greater when the there is a greater amount of the substance in the environment 20.

Note that the dot array 29 depicted by FIG. 3 completely covers the end of the core 23 and extends onto the cladding 25 around the edges of the core 23. Thus, the light in the core 23 strikes the dots 27 and reflects back through the core 23 at varying intensities depending on the resonance frequency of the dot array 29. Due to the location of the dot array 29 directly on the tip of the optical fiber 12 over the core 23, optical alignment between the optical fiber 12 and the test environment 20 is not required thereby avoiding significant drawbacks plaguing conventional LSPR sensors. Accordingly, an LSPR sensor that is relatively lightweight, portable, and easy to use is provided.

Figure 4:
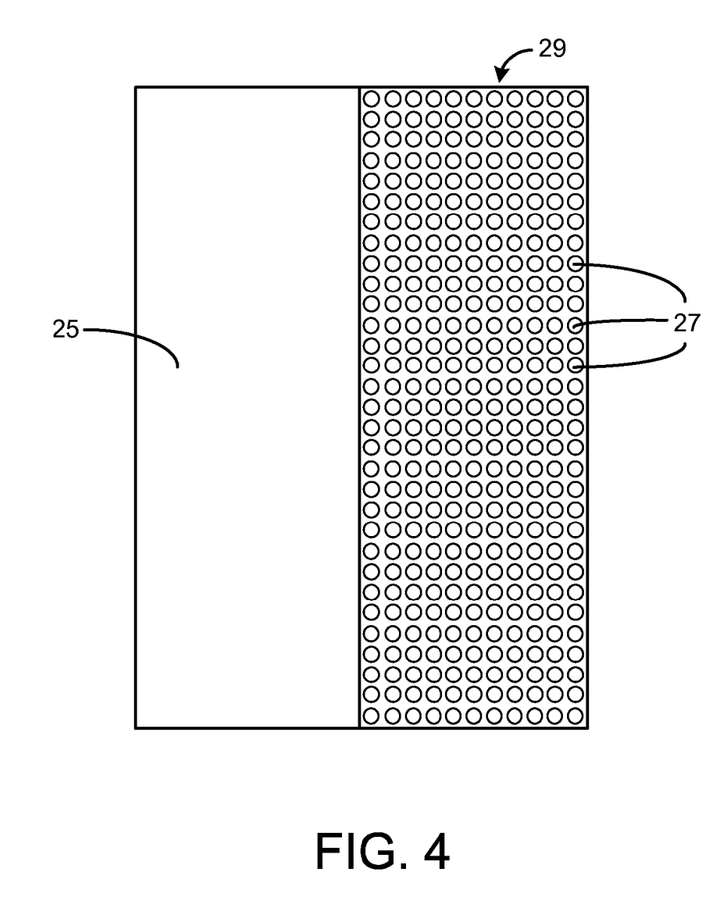
FIG. 4 depicts a close up view of an edge of the dot array of FIG. 3.

FIG. 4 depicts a close up view of an edge of the dot array 29 of FIG. 3. As set forth above, the dot array 29 comprises a plurality of spaced-apart dots 27 positioned directly on the flatly cleaved tip of the optical fiber 12. Specifically, the dots 27 are positioned directly on the tip of the core 23 (FIG. 2) and cladding 25. The size and material composition of the dots 27, as well as the spacing between the dots 27, may differ in different embodiments depending on application specifications. By controlling the chemical functionalzation of the dots 27, a user can control which substance causes a shift in the measured absorption peak and also the extent of the shift for a given concentration or amount of the substance. Thus, the dot array 29 can be designed to detect a specific substance of interest.

If desired a plurality of optical fibers 12 can be bundled together and simultaneously or otherwise exposed to the test environment 20 in order to test for a plurality of substances. In this regard, the dot array at the end of each such fiber 12 is configured to detect a different substance of interest relative to the dot arrays of the other fibers 12. Specifically, one fiber 12 can be used to detect a first substance of interest, and another fiber 12 with a different dot array configuration can be used to detect another substance of interest. Alternatively, the same dot array 29 configuration on each fiber tip can be chemically functionalized differently according to each substance of interest in the test environment. In such an embodiment, multiple absorption peaks may be present in the returned spectrum where the wavelength of each absorption peak indicates whether and to what extent a respective substance in the in the test environment. Thus, the exemplary LSPR system 10 can be easily scaled to detect a large number of substances, if desired.

In one embodiment, the dots 27 are formed on the tip of the optical fiber 12 using electron beam lithography (EBL) techniques, discussed in more detail hereafter, although other methods of forming the dots 27 on the tip of the optical fiber 12 are possible in other embodiments. Each dot 27 is substantially the same height and diameter. In one embodiment, each dot 27 has a diameter of about 190 nm and a height of about 55 nm, although other dimensions are possible in other embodiments.

Figure 5:
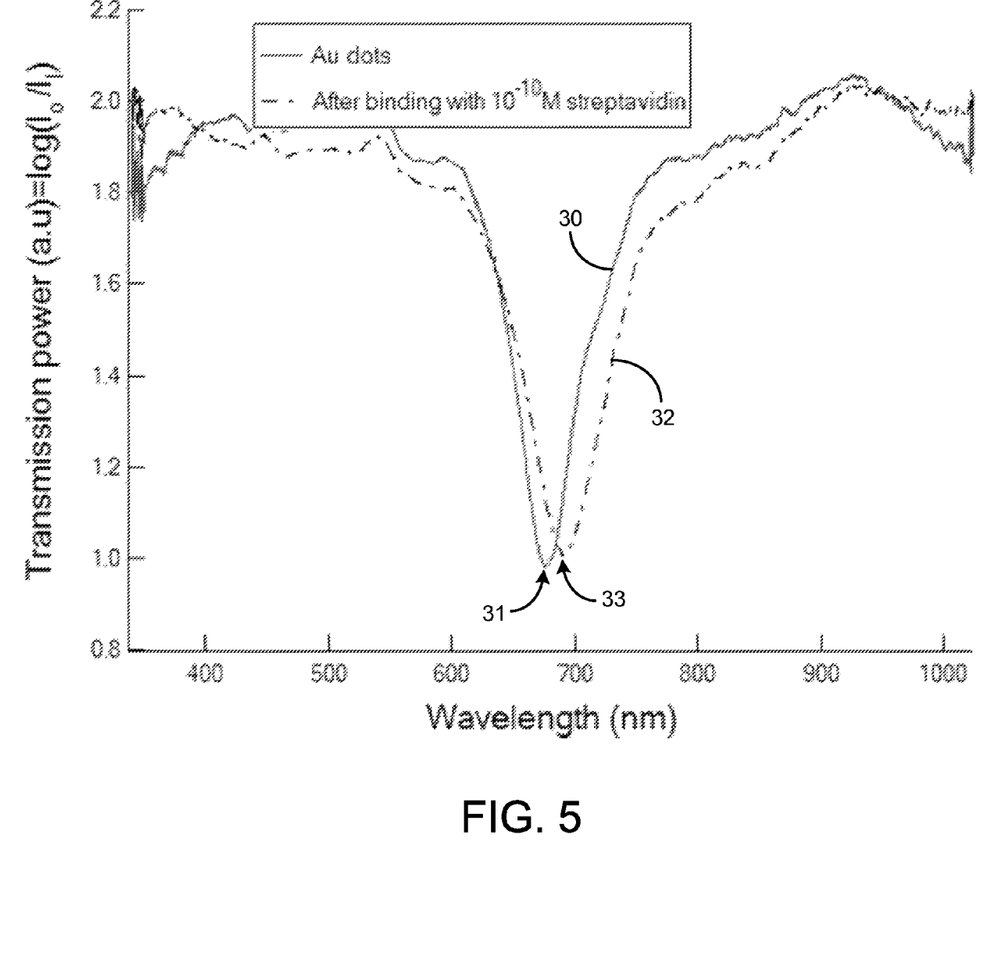
FIG. 5 is a graph illustrating a shift in absorption peak due to the presence of streptavidin.

FIG. 5 is a graph illustrating a wavelength shift in absorption peak between a measured transmission spectrum and a reference transmission spectrum for reflected light. An experiment for detecting streptavidin was conducted using a tungsten halogen white light source. Gold dots 27 (FIG. 2) on the optical fiber tip were functionalized by chemically combining the gold dots with biotin so that the dots had a desired affinity for streptavidin. A spectrometer 17 (FIG. 1) was used to measure a reference transmission spectrum 30 of light reflected through the optical fiber 12 (FIG. 1) from the gold dots 27. The reference transmission spectrum 30 was measured between the wavelengths of 400-1000 nanometers (nm). A reference absorption peak 31 was measured at a wavelength of approximately 680 nm when no streptavidin was present.

After the reference absorption peak 31 was determined, $10^{-10}$ molar (M) of streptavidin was introduced into the test environment 20 (FIG. 1). Gold dots 27 were again functionalized with biotin and used on the optical fiber tip due to their affinity for binding with streptavidin. The spectrometer 17 was used to determine a measured reflection spectra 32 for the reflected light between the wavelengths of 400-1000 nm, and a measured absorption peak 33 was determined at a wavelength of approximately 695 nm. Thus, a shift of approximately 15 nm in the measured absorption peak 33 as compared to the reference absorption peak 31 was observed. Accordingly, the presence of streptavidin was determined based on the shift between the reference absorption peak 31 and the measured absorption peak 33.

FIGS. 6-11 depict a tip of an optical fiber 12 during an exemplary manufacturing process for forming the dot array 29 on the tip of the optical fiber 12 using EBL techniques. Note that other techniques for forming the dot array 29 on the tip of the optical fiber 12 are possible in other embodiments.

Figure 6:
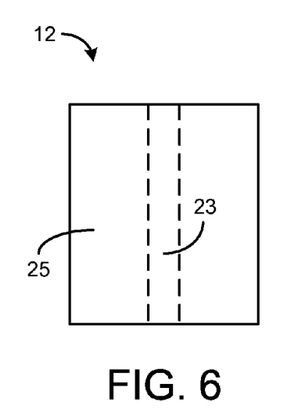
FIG. 6 depicts a tip of an optical fiber, such as is depicted by FIG. 2, before a dot array is formed thereon.

FIG. 6 depicts a side view of the optical fiber 12. An outer buffer coating on the optical fiber 12 is removed. In one embodiment, the outer buffer coating is removed using a stripper, although other methods of removing the coating are possible in other embodiments. The tip of the optical fiber 12 is cleaved generally perpendicularly to produce a flat end face of the fiber 12, as shown in FIG. 6. Once the tip of the optical fiber 12 is flatly cleaved, a thin layer of material (not shown) is deposited on the tip for adhesion. In one embodiment, the layer is approximately 2 nm thick and comprises chromium, although other thicknesses and materials are possible in other embodiments. The chromium layer is deposited such that it completely covers an end of the core 23. In one embodiment, the chromium layer is deposited using a vacuum sputtering method. However, other methods for depositing the chromium layer are possible in other embodiments.

Figure 7:
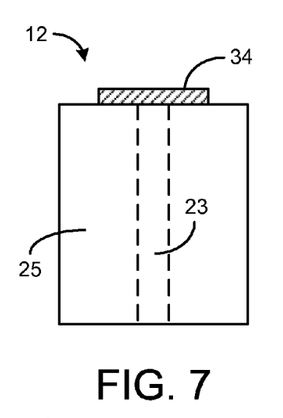
FIG. 7 depicts the fiber tip of FIG. 6 after a metallic film is formed on the tip.

FIG. 7 depicts the fiber tip of FIG. 6 after a metallic film 34, such as, for example, gold, is deposited on top of the chromium layer. In one embodiment, a Denton sputter system is utilized to deposit the gold film 34, although other techniques are possible in other embodiments. The gold film 34 completely covers an end of the core 23 with portions of the film 34 extending past the core 23 and covering portions of the cladding 25. In this regard, precise alignment of the gold film 34 and the core 23 is unnecessary.

In one embodiment, the film 34 is approximately 55 nm thick, although other thicknesses are possible in other embodiments. The gold film 34 has a substantially uniform thickness, as shown by FIG. 7, in order to facilitate uniformity among the dots 27 (FIG. 2) for purposes of LSPR. Changes in the thickness of the dots 27 result in changes in the optical properties of the dots 27 when the dots 27 are excited by light. Thus, substantially uniform thickness of the film 34 is generally desirable.

Figure 8:
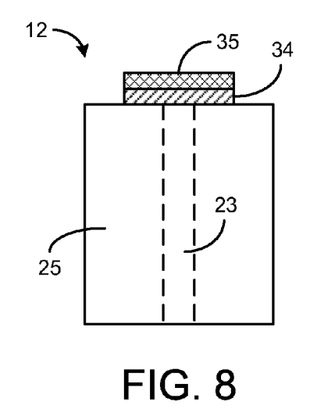
FIG. 8 depicts the fiber tip of FIG. 7 after a resist layer is formed on the tip.

FIG. 8 depicts the fiber tip of FIG. 7 after resist material 35, such as, for example, ZEP 520A, is coated on top of the gold film 34, though other resist material may be used in other embodiments. In one embodiment, the resist material 35 is applied by dipping the tip of the fiber 12 in an electron beam (e-beam) resist solution and positioning the fiber 12 in a clamp (not shown) in a straight upward position with the resist material 35 positioned on top. A "vibration coating" technique is then used to get rid of extra liquid resist material 35 and achieve a substantially uniform thickness coating layer on top of the gold film 34. Such vibration coating technique involves mechanically vibrating the tip of the fiber 12 in order to shake off the excess liquid e-beam resist. The strength and frequency of the vibration may be adjusted depending on the length of the fiber 12 above the clamp and the initial displacement of the fiber tip.

Once vibration coating of the resist material 35 is complete, the tip of the fiber 12 is baked in an oven in order to harden the resist material 35. In one embodiment, the fiber tip is baked at approximately 120 degrees Celsius (C) for about 30 minutes, although other temperatures and times are possible in other embodiments. Such baking hardens the resist material 35 in a generally uniform thickness. In one embodiment, the thickness of the resist material 35 is in the range of approximately 80 nm to 100 nm, although other thicknesses are possible in other embodiments.

Figure 9:
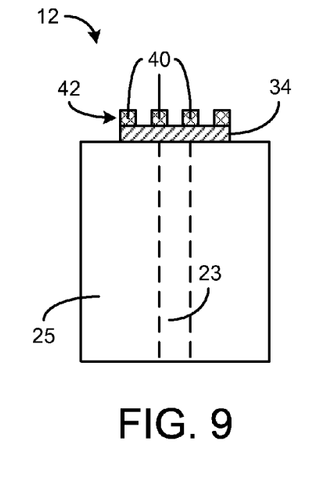
FIG. 9 depicts the fiber tip of FIG. 8 after the resist layer is patterned according to the desired dot array.

FIG. 9 depicts the fiber tip of FIG. 8 after resist dots 40 forming resist array 42 are formed in the desired pattern of the dot array 29 (FIG. 2). In one embodiment, the resist dots 40 are formed using an EBL process, but other processes may be used in other embodiments. The resist dots 40 are formed in the desired pattern of the dot array 29 using a field emission scanning electron microscope (not shown). In one embodiment, a voltage of approximately 30 kilovolts (kV) and a dose of approximately 70 micro-Coulombs per square centimeter ($\mu C/cm^2$) are used, although other values are possible in other embodiments.

After the resist array 42 is formed, the tip of the fiber 12 is developed. The fiber tip is developed by dipping the tip in e-beam resist developer, such as, for example, ZEP N50. In one embodiment, the tip is dipped in e-beam resist developer for about one minute and rinsed with deionized water for about one minute, although other time periods are possible in other embodiments. After developing, the resist array 42 is dehydrated and hardened. In one embodiment, the resist array 42 is dehydrated and hardened by drying the fiber tip with a pure nitrogen stream and baking the fiber tip in an oven at approximately 120 degrees C. for 30 minutes. However, other methods for dehydrating and hardening the resist array 42 are possible in other embodiments.

Figure 10:
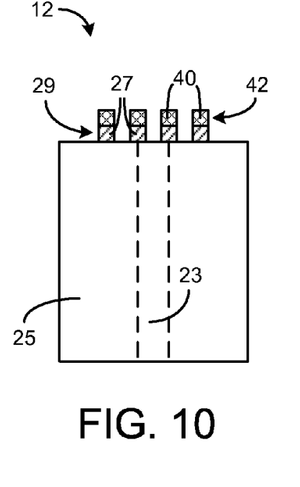
FIG. 10 depicts the fiber tip of FIG. 9 after the metallic film is etched.

FIG. 10 depicts the fiber tip of FIG. 9 after the gold film 34 (FIG. 7) is etched thereby forming the dot array 29 in the pattern of the resist array 42. In one embodiment, the pattern of the resist array 42 is transferred to the gold film 34 using a reactive ion etching (RIE) etch technique with Argon ions. In such embodiment, the etch time may be approximately 3.5 minutes, the platen power may be approximately 200 watts (W), and the argon gas flow rate may be approximately 20 standard cubic centimeters per minute (sccm). However, other etching techniques are possible in other embodiments. The gold film 34 is etched out around the resist dots 40 in spaces between the dots 40 in order to form the dot array 29 in the same pattern as the resist array 42. The gold film 34 is completely removed from between the dots 40 in order to separate the dots 27 from one another. Thus, the dot array 29 has an identical pattern to the resist array 42.

Figure 11:
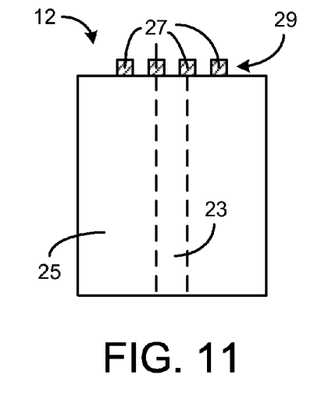
FIG. 11 depicts the fiber tip of FIG. 10 after the resist material is completely removed.

FIG. 11 depicts the fiber tip of FIG. 10 after the resist dots 40 (FIG. 9) are removed. In one embodiment, the resist dots 40 are removed by dipping them in a substance for removing e-beam resist, such as, for example, acetone for approximately one minute. However, other substances for removing the dots 40 are possible in other embodiments. Furthermore, the period of time for dipping the resist dots 40 in the substance for removing the dots 40 may vary in other embodiments. For example, in one alternative embodiment, the dots 40 are submerged in the substance overnight in order to ensure complete removal of the dots 40.

Once removal of the resist dots 40 is complete, the dot array 29 remains on the tip of the optical fiber 12. Annealing the dot array 29 in a high temperature (e.g., approximately 300 degrees C. to 500 degrees C.). Accordingly, an LSPR sensor comprising the metallic dot array 29 on the tip of the optical fiber 12 is provided. Other methods for forming the dots 27 on the tip of the optical fiber 12 are possible in other embodiments.

In one exemplary embodiment, assume that the dot array 29 is arranged to have an affinity for a particular substance of interest. Prior to testing, the system 10 is calibrated by running a test when the tip of the optical fiber 12 having the dot array 29 is exposed to an environment known to be free of the substance of interest. In this regard, white light is transmitted from the light 14 through the coupler 15 into the core 23 of the optical fiber 12. Such light ultimately strikes the dot array 29 causing surface plasmons of the dot array 29 to resonate resulting in an absorption peak at a certain wavelength. The light reflects back through the fiber 12 to the spectrometer 17, which measures the wavelength of the absorption peak. Data indicative of the wavelength of such peak is transmitted to the control logic 19, which stores such data for use later in testing, as will be described in more detail hereafter.

During testing, the tip of the optical fiber 12 having the dot array 29 is placed into the test environment 20. The light source 14 transmits white light through the coupler 15 to the optical fiber 12, as shown by block 100 of FIG. 12. The light travels through the core 23 of the optical fiber 12 until the light reaches the tip of the optical fiber 12, where illumination from the light excites surface plasmons of the dots 27 thereby causing the surface plasmons to resonate, as shown by block 102. For illustrative purposes, assume that the substance of interest is not present in the test environment 20.

Because the substance of interest is not present in the test environment 20, the resonance frequency of surface plasmons of the dots 27 should be approximately the same as the resonance frequency of such surface plasmons during calibration resulting in an absorption peak at about the same wavelength as during calibration. After striking the dot array 29, the light is reflected back through the core 23 to the spectrometer 17 via the coupler 15, where the spectrometer 17 detects the light and measures the absorption peak of the light, as shown by block 104. The spectrometer 17 measures the absorption peak and provides data indicative of the wavelength of the absorption peak, which analyzes such data to determine whether the substance of interest is present in the environment, as shown by blocks 106 and 108 of FIG. 12. Since substance of interest is not present in the test environment 20 in the current example, there is no shift in the measured absorption peak during testing as compared to the absorption peak during calibration. Accordingly, the control logic 19 determines that the substance of interest is not present in the test environment 20 and displays information indicative of such determination.

Figure 12:
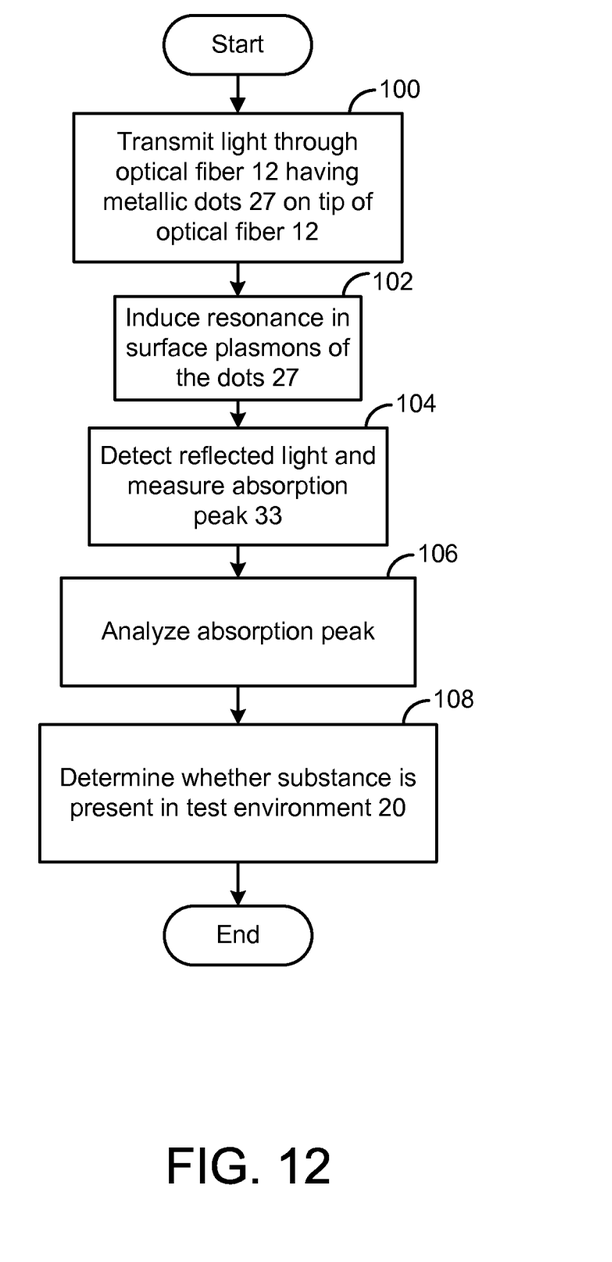
FIG. 12 is a flowchart depicting an exemplary method for using an LSPR sensing system, such as is depicted by FIG. 1.

Now assume that the substance of interest is present in the test environment 20 during testing. The same process described above occurs except that the wavelength of absorption peak measured by the spectrometer 17 is different during testing relative to the such wavelength during calibration. That is, the wavelength of the absorption peak shifts when the fiber tip is exposed to the test environment 20. Based on the measured wavelength difference of the absorption peak, the control logic 19 detects the presence of the substance of interest. The control logic 19 also determines an extent to which the substance is present based on such difference. The control logic 19 then displays information indicative of the detection and an estimation of the amount of the substance that is present in the test environment 20.

Now therefore the following is claimed:

1. A localized surface plasmon resonance (LSPR) sensing system, comprising:
   a light source configured to transmit light;
   an optical fiber having a metallic dot array on an end face of the optical fiber, the optical fiber having a core surrounded by cladding, the core extending from the end face, the dot array having an affinity for at least one substance, wherein the optical fiber is optically coupled to the light source such that the light passes through the core and is guided by the core and the cladding to the end face, and wherein the metallic dot array is positioned over the core such that the light guided by the core and the cladding strikes the dot array, the dot array further having surface plasmons which resonate when illuminated by the light;
   a spectrometer configured to receive the light from the optical fiber and to measure an absorption peak of the light; and
   control logic configured to detect whether the substance is present based on the measured absorption peak.

2. The LSPR sensing system of claim 1, wherein the control logic is configured to detect whether the substance is present based on a wavelength of the measured absorption peak.

3. The LSPR sensing system of claim 1, wherein the control logic is configured to estimate an amount of the substance within a test environment based on a wavelength of the measured absorption peak.

4. The LSPR sensing system of claim 1, wherein the end face is flat.

5. The LSPR sensing system of claim 1, wherein the core is perpendicular to the end face.

6. The LSPR sensing system of claim 1, wherein the control logic is configured to estimate an amount of the substance at the end face based on a wavelength of the measured absorption peak.

7. A method for detecting substances based on localized surface plasmon resonance (LSPR), comprising the steps of:
    transmitting light;
    guiding the light through a core of an optical fiber to an end face of the optical fiber from which the core extends, the optical fiber having a metallic dot array on the end face;
    inducing resonance in surface plasmons of the metallic dot array via the light;
    detecting the light;
    measuring an absorption peak of the detected light;
    determining, via control logic, whether a substance is present at the end face based on the measured absorption peak; and
    displaying, via a display device, information based on the determining step.

8. The method of claim 7, further comprising determining, via the control logic, an amount of the substance at the end face based on a wavelength of the measured absorption peak.

9. The method of claim 7, wherein the end face is flat.

10. The method of claim 7, wherein the end face is perpendicular to the core.

* * * * *

UNITED STATES PATENT AND TRADEMARK OFFICE
CERTIFICATE OF CORRECTION

Page 1 of 1

PATENT NO. : 8,879,065 B1
APPLICATION NO. : 13/104719
DATED : November 4, 2014
INVENTOR(S) : Yongbin Lin, Robert Lindquist and Yang Zou It is certified that error appears in the above-identified patent and that said Letters Patent is hereby corrected as shown below:

In the Specification

Column 1, line 3, insert the following text:

-- STATEMENT REGARDING FEDERALLY SPONSORED RESEARCH OR DEVELOPMENT

This invention was made with Government support under NNM06AA05G awarded by the NASA. The Government has certain rights in the invention. --

Signed and Sealed this
Seventh Day of July, 2015

Michelle K. Lee
*Director of the United States Patent and Trademark Office*